United States Patent [19]

Harris, Sr. et al.

[11] 4,010,648
[45] Mar. 8, 1977

[54] ADAPTER UNIT FOR USE IN SAMPLING FLUID SPECIMENS

[76] Inventors: Rano J. Harris, Sr., 1945 Carolyn Sue Drive, Baton Rouge, La. 70815; Julius P. Averette, Jr., 4332 Delaware St., Baton Rouge, La. 70805

[22] Filed: Oct. 1, 1975

[21] Appl. No.: 618,373

[52] U.S. Cl. .............................. 73/423 R; 23/292; 73/425.4 R; 141/369
[51] Int. Cl.² ......................................... G01N 1/14
[58] Field of Search ... 73/421 R, 422 GC, 421.5 R, 73/423 R, 422 R, 425.4 R; 141/25, 369; 23/292

[56] References Cited
UNITED STATES PATENTS

| | | | |
|---|---|---|---|
| 2,752,228 | 6/1956 | Gould | 73/427 R X |
| 3,137,174 | 6/1964 | Hawk et al. | 73/422 GC X |
| 3,559,703 | 2/1971 | Maul | 73/422 GC X |
| 3,776,042 | 12/1973 | Werra et al. | 73/422 R |
| 3,901,413 | 8/1975 | Harris | 222/309 |
| 3,915,677 | 10/1975 | Oppegaard | 73/422 GC X |

*Primary Examiner*—Richard C. Queisser
*Assistant Examiner*—Daniel M. Yasich
*Attorney, Agent, or Firm*—Llewellyn A. Proctor

[57] ABSTRACT

An adapter unit, or apparatus for the receipt and containment of a fluid specimen sample under sub-atmospheric or supra-atmospheric pressure. The device is useful in facilitating the transfer of the fluid specimen to a fluid injector device, or needle syringe. In one form, the device is comprised of a valved, closed container the wall of which is fitted with oppositely disposed tubular seals within which is contained a reciprocable plunger. In another form, the device is constituted as an adapter unit which can be adjoined with a valved container for taking a sample therefrom, and subsequently separated therefrom, as desired. In either form, a yoke-like member or C-shaped frame is provided as an overall and necessary part of the combination. One end of the C-shaped frame is secured to a side of the reciprocable plunger, and the other end thereof is provided with a guide or holder. The fluid injector device or syringe can be placed within the holder, and held, such that the needle portion thereof can, in an initial positioning, be partially inserted into the axial opening of a seal adjacent to an end of the reciprocable plunger of the closed container which also lies therein, such that movement of the C-frame will shift the plunger and holder in unison. By such action, the plunger will be moved from the axial opening of the seal and its presence replaced by the needle portion of the fluid injector or syringe. The dispensing end of the needle by such action will be advanced and immersed within the fluid specimen within the container. A fluid specimen can thus be withdrawn at container pressure, locked and stored within the fluid injector device, or syringe, for subsequent injection.

10 Claims, 4 Drawing Figures

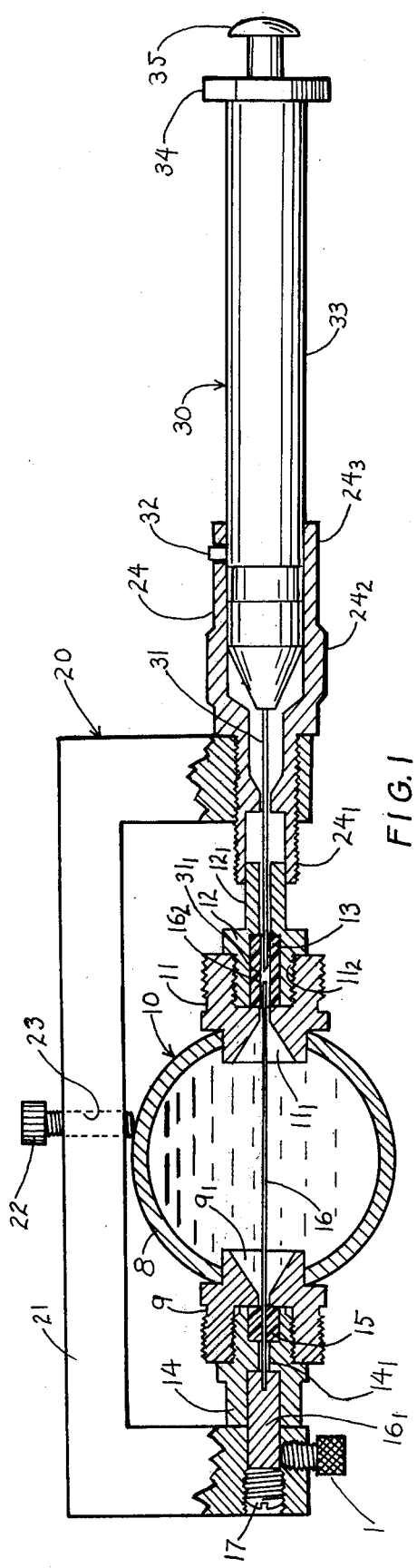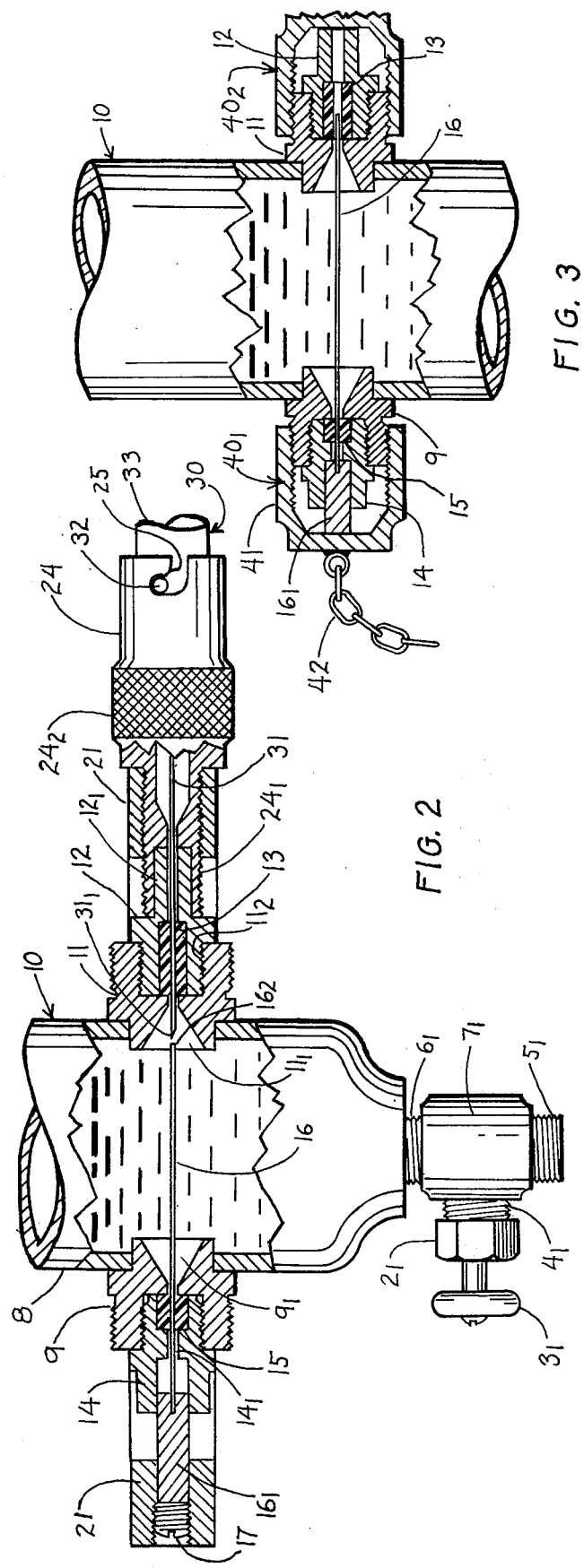

ADAPTER UNIT FOR USE IN SAMPLING FLUID SPECIMENS

There has long been a need in the art to provide apparatus, or means, suitable for the withdrawal of fluids. i.e., gases or liquids, from sources wherein they are contained under extremely low or ultra high pressures. Thus, e.g., it is very common for liquids to be confined within operating units or vessels, under extremely high pressure ranging up to several hundred pounds per square inch, i.e., 500 pounds per square inch, and higher. Whereas it is very desirable to withdraw liquids into a specimen container without change in composition such that a sample representative of that contained under pressure is obtained, this is not generally accomplished with ease, if at all. Prior art devices are unsuitable for such use because they are unable to withstand the low or ultra high pressures without leakage, and even relatively low leakage creates intolerable error in the handling of relatively small quantities of the fluid specimens. Even more important, errors in the measurement of the actual volume of sample, or in the composition intended for analysis are particularly significant. Present methods for obtaining fluid specimens from ultra low and ultra high pressure sources are complex, require considerable operator time for their usage, and leave much to be desired in terms of their accuracy and precision.

It is nonetheless a primary objective of the present invention to obviate these disadvantages and provide a new and improved fluid sampling device, or device capable of facilitating the withdrawal and measurement of fluid specimens from sub-atmospheric and pressurized sources with high precision and accuracy.

A specific object of the invention is to provide a device of such character which is particularly useful for facilitating the withdrawal and storage, if desired, of gaseous specimens, or volatile liquid specimens in composition and form truly representative of the source from which they were taken; and which device is capable of facilitating the measurement and transfer of such specimens to fluid injection devices, or syringes, on the order of only about 0.01 to about 5 microliters, or fractional parts thereof.

A further object of the invention is to provide a device of simple construction in which the parts are small in number and can be easily and quickly assembled or reassembled, thereby minimizing the cost of manufacture.

These objects and others are achieved in accordance with the present invention constituting an adapter unit, inclusive in one of its forms of a specially adapted closed container unit for holding a fluid specimen under high pressure or vacuum, and an injector guide assembly which facilitates withdrawal of fluid specimen via use of a fluid injection device, or needle syringe which per se forms no part of the invention. In another of its forms, the adapter unit is constituted as a separate unit from the container but can be adjoined with a valved container unit for taking a sample therefrom, and subsequently separated therefrom, as desired.

The specially adapted container, which in one embodiment forms a part of the overall adapter unit, is a closed vessel, the wall, or walls, of which is fitted with oppositely disposed tubular seals through the axial openings of which is mounted a reciprocable shaft or plunger. In one position, the plunger is extended through the axial openings of both tubular seals such that the contents of the container are sealed. In another position, constituting the sampling position, the movable shaft or plunger is moved from the axial opening of one of the seals, and on entry of the needle of an injection device, or syringe, which follows the retreating shaft or plunger, the dispensing end of the needle can be projected into the fluid such that a fluid specimen can be withdrawn at container pressure. On withdrawal of the needle of the injection device, or syringe, the retreating needle is replaced within the axial opening of the seal by the plunger to retain the seal, the plunger again sealing by its physical presence through both tubular seals.

In a second embodiment, the seals and plunger are constituted as a part of a tubular member which forms an adapter unit which can be adjoined to a valved container. In this form, the adapter unit is used to take a sample from the valved container. The adapter unit and container, on the other hand, can be used in combination for taking a sample from a supply source.

The injector guide assembly, which forms a part of the overall adapter unit, in either of its forms, is constituted of a yoke-like member, or C-shaped frame, one end of which carries a socket-like tubular receptacle, guide or holder and the other of which is provided with means for engagement with the plunger of the adapter unit, or specially adapted container unit. The socket-like tubular receptacle, guide, or holder, is adapted to carry the injection device or syringe, as well as can be slidably mounted upon one of the tubular seals of the adapter, or specially adapted container unit such that the needle portion of the injection device or syringe can be guided into and projected through the axial opening of said seal. Movement of the frame moves the plunger of the adapter, or specially adapted container unit, and socket-like tubular receptacle (and consequently an injection device or syringe inserted therein) in unison such that the needle of the injection device or syringe can replace the retreating plunger such that the dispensing end of the injection device, or syringe, can be immersed within the fluid, and a fluid specimen can be withdrawn into the barrel of the injection device or syringe, without breaking the seal.

These and other salient features and advantages of the invention will be better understood by reference to the following detailed description which makes specific reference to the attached drawings. In the drawings, similar numbers are used to represent similar parts, or components, and subscripts are used to refer to subportions of a part, and to identical parts, illustrated or not specifically illustrated.

Referring to the drawings:

FIG. 1 depicts a partial cross-section view of a first preferred type of adapter unit, inclusive of a specially adapted cylindrical container (end view), of which it is an integral part, and injector guide assembly (elevation view), useful with a fluid injector, or syringe, for obtaining samples of fluid specimens, notably liquid contained under high pressure or high vacuum.

FIG. 2 further depicts a partial cross-sectional view of the adapted unit illustrated by the preceding figure, inclusive of said cylindrical container (side view) and injector guide assembly (edge view).

FIG. 3 depicts a fractional side view of the specially adapted container described by reference to FIGS. 1 and 2, with devices employed for protection of adapted features.

Figure 4:
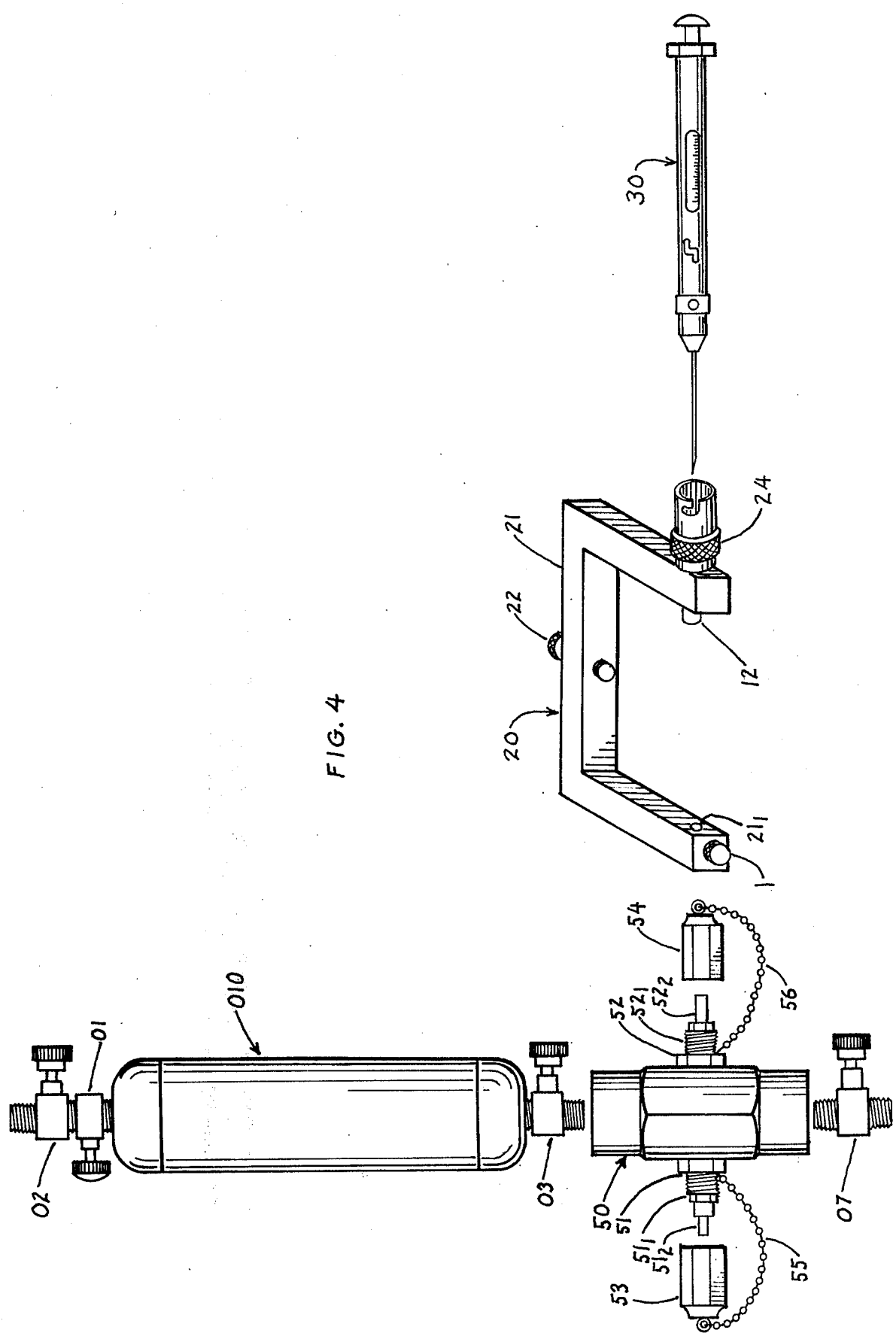
FIG. 4 depicts a second preferred embodiment wherein the adapter unit is constructed separate and apart from the container to which it can be adjoined and then utilized, in combination with an injector guide assembly as described by FIGS. 1 and 2. The several parts are shown unassembled.

Referring generally to FIGS. 1–3, but in this first instance noting particularly FIGS. 1 and 2, there is described a complete adapter unit inclusive of a specially adapted cylindrical container 10 and an injector guide assembly 20. The container 10 is conventional in design, except as relates to particular features by virtue of which it is adapted for use in sampling fluid specimens (liquid or gas) in concert with injector guide assembly 20. The ends of container 10 are generally provided with entry and exit means, or valves, by virtue of which a fluid, e.g., a liquid from a source can be passed therethrough, the exit means closed to trap the fluid and permit it to approach static equilibrium at the pressure of the source, after which time the entry means are closed to maintain the fluid specimen at static equilibrium. The entry and exit means can be similar in design and function.

The exit means in its most practical form embodies a valve, e.g., a gate type valve, suitably as depicted by reference to FIG. 2. The lower end of the container 10 is tapered inwardly, tapped and internally threaded and a valve comprised of a body $7_1$, and externally threaded tubular portions or nipples $6_1, 5_1$ provide entry and exit features, respectively, through the valve. The nipple $6_1$ secures the valve body $7_1$ to the end of the container 10, and the valve is opened and closed by virtue of valve stem $3_1$. The valve per se is of entirely conventional construction, and packings, washers and the like can be changed out by removal of the stem $3_1$ which is held in place within the valve body $7_1$ by virtue of an access cap $2_1$ threadably engaged with externally threaded nipple $4_1$. Suitably, and preferably, a similar type valve (not shown) is fitted upon the opposite end of cylindrical member 10. By virtue of such valve, the cylindrical member 10 can be connected to a larger vessel, or inlet to such vessel, constituting a supply source for the fluid specimen to be sampled, as via a suitable internally threaded tap to which a nipple $5_2$ (not shown) is threadably engaged.

The walls 8 of cylindrical container 10 are specially adapted with means which make cylindrical container 10 suitable for use in sampling fluid specimens in concert with injector guide assembly 20. The walls 8 are thus provided with oppositely disposed, similarly designed tubular members 9,11, the outwardly projecting ends of which are both internally and externally threaded. The depth of the internally threaded portion of these members 9,11 is limited and ends to provide a flat seating surface, or face, and the smaller axial opening at the face of each of the members 9,11 diverges from the central, or axial opening to form an inwardly directed frusto conic shaped opening $9_1, 11_1$. Smaller diameter tubular members 14,12, respectively, are fitted within tubular members 9,11, the nature of each of which is described in the paragraphs immediately following.

The small diameter tubular member 12 is provided with a narrow diameter projecting portion $12_1$ having a smooth external surface. The central portion of member 12 is flanged, the opposite end is externally threaded, and the externally threaded end is threadably engaged and seated within the opening $11_2$ of the larger diameter member 11. The inwardly faced side of tubular member 12 is provided with a tubular shaped recess adjoining an axial opening, and a tubular shaped seal 13 is contained therein. The axial openings of seal 13, and tubular members 11,12 are all aligned.

The small diameter tubular member 14, like tubular member 12, is provided with an externally threaded end by virtue of which it is threadably engaged with, or coupled to, the larger diameter tubular member 9, and an internal inwardly facing cylindrical shaped opening located therein is provided with a tubular seal 15. The opposite end of the tubular member 14 is also provided with an internal cylindrical shaped opening which is in communication with the axial opening $14_1$ of tubular member 14, and the axial opening of seal 15, and within which is contained a reciprocably movable shaft, or handle, $16_1$ on the forward end of which is mounted a solid plunger 16. The plunger 16, it will be observed, is fitted through the aligned axial opening $14_1$, the axial opening through seal 15, the axial opening through member 9, and frusto conic shaped opening $9_1$. It is also aligned upon, and extendable into, the axial opening through tubular member 11, and can be moved into and out of the axial opening of seal 13, which is located within tubular member 12.

The container 10 per se can be transportable or permanently mounted at a location wherein samples of fluid specimens are periodically taken, e.g., as upon suitable condensation or the liquid collection tank of a distillation column, autoclave, or unit operated at sub-atmospheric or supra-atmospheric pressures. In either event, the injector guide assembly 20 need not be permanently mounted upon the container 10. Accordingly, removable protective caps $40_1, 40_2$, as described by reference to FIG. 3, can be located upon the oppositely disposed tubular members 9,11 to protect and essentially cover these members, tubular members 12,14 mounted therein, and also the plunger 16. The open ends of protective caps $40_1, 40_2$ are thus internally threaded, and threadably engagable with the externally threaded tubular members 9,11. Suitably, chains of sufficient length, e.g., a chain 42, can also be used to secure the caps $40_1, 40_2$ (e.g., to the body of cylinder 10) to avoid loss or misplacing of the caps $40_1, 40_2$. This can be done without interfering with the normal function of these members, as during transport from sampling point to test point.

The injector guide assembly 20, best described by reference to FIG. 1, is characterized generally as a yoke-like member, or C-shaped frame 21, one end of which is provided with a socket-like tubular receptacle, holder, or inlet 24, within which a fluid injection device or syringe 30 can be inserted, and the other end of which is engageable with handle $16_1$ of plunger 16 by tightening down the thumb screw 1. The inlet 24, in its preferred form, is comprised of a small diameter externally threaded forward end which is threadably engaged within an internally threaded tapped opening within a terminal end of the C-frame 21 which secures the member in place upon the frame. The extreme forward end $24_1$ of the inlet 24 is provided with an internal cylindrical shaped opening which fits over, mates with, and provides a slip-fit with projection $12_1$ of tubular member 12. These members are thus movable, one relative to the other, to the extent that projection $12_1$ can be moved before it is blocked by contact with the end wall, or face, formed at the end of the opening. The central portion of inlet 24 is somewhat enlarged, and its surface is knurled $24_2$ (FIG. 2). The opening at the forward end of the inlet $24_1$ is adjoined, through a small axial opening, with the larger openings at the rearward end of the inlet 24, this end of the inlet 24 being designed to act as a receptacle and carrier device for a fluid injection device, or syringe 30. The other end of the C-frame 21 is provided with an opening within which is snugly fitted the handle $16_1$ of plunger 16, which is held in place by the thumb screw 1. Additionally, a set screw 17 is provided as a safety device to prevent loss of sample if the C-frame is moved and the thumb screw 1 happens to become loose. Closure of the container 10 is assured by movement of plunger 16, anytime the C-frame 21 is moved to the right. A further set screw, or thumb screw 22 is located, and threadably engaged via suitable threads, within an opening 23 located at about the mid-point of the C-frame 21. The purpose of set screw 22 is to limit, or prevent, movement of the C-frame 21 to the left beyond a certain point when its lower end is projected downwardly as in FIG. 1. On the other hand, the set screw 22 permits free movement of the C-frame 21 when its lower end is raised into the C-frame 21 so that it cannot contact wall 8 of cylinder 10, such as is necessary to reposition the C-frame as shown by reference to FIG. 2. And, of course, the C-frame can be locked in the position shown by reference to FIG. 2 on again lowering the end of the set screw 22 into contact with wall 8 on the opposite side of the cylinder 10.

The syringe 30 per se forms no part of the present invention, but is of a special high pressure valved type particularly useful in sampling fluid specimens with the specialized adapter unit described herein. The nature and function of this syringe is fully described by reference to U.S. Pat. No. 3,901,413 issued Aug. 26, 1975, the disclosure of which is herewith incorporated by reference. Suffice it to point out briefly that the syringe 30 includes the usual needle 31, barrel 33, and plunger 35 located adjacent the flange 34. An accurately measured fluid specimen withdrawn from a supply source can be locked and sealed within the syringe.

In operation, referring specifically to FIG. 1, the dispensing end $31_1$ of needle 31 is inserted partially through the axial opening within tubular seal 13. In such position, it will also be observed that the dispensing end $31_1$ of needle 31 lies only a short distance from the tip $16_2$ of plunger 16, and also within the axial opening of tubular seal 13. To accomplish such positioning, C-frame has thus been shifted to its extreme rightward position, this moving plunger handle $16_1$ its maximum extent into the internal cylindrical opening within tubular member 14, and to maintain such positioning, the lower end of set screw 22 has been lowered into contact with wall 8 so that the C-frame 21 is locked in this position. In such position, the liquid contents of the cylinder 10 are completely sealed in place.

In such position the syringe 30 is locked in place via lug 32 which is turned into the upward portion of notch 25 of inlet 24 (note FIG. 2). Syringe 30 is thus secured within inlet 24 which also acts as a receptacle and carrier device for the syringe. To take a liquid specimen from the container 10, screw 22 is rotated to raise the lower end thereof out of contact with wall 8 of the container. The C-frame 21 is then shifted to the left, this repositioning necessarily moving plunger 16 and syringe 30 in unison. On relowering the lower end of set screw 22 into contact with wall 8 of cylinder 10, the adapter unit and consequently syringe 30 are locked in place and the unit is ready for taking a sample, as depicted by reference to FIG. 2.

With reference to FIG. 2, it will be observed that the dispensing end $31_1$ of needle 31 has now been projected into the body of liquid. Retraction of the plunger 35 will withdraw an accurately measured quantity of the specimen from the container 10, which specimen can then be locked and held within the syringe 30. On repositioning of the C-frame 21 as depicted by reference to FIG. 1, the syringe 30 can be withdrawn, and the fluid specimen injected or stored as desired.

A preferred type of adapter unit, for use in combination with a valved container, is described by reference to FIG. 4. Referring generally to FIG. 4 there is shown an adapter 50, comprised of a tubular member within the wall of which is provided a pair of oppositely disposed tubular seals 51,52 which can be the same in design and function as those described by reference to FIG. 1–3. The inward or intermediate portions $51_1, 52_1$ of these seals 51,52 are externally threaded for receipt of open-end internally threaded caps 53,54 which can be chained to said adapter 50 via chains 55,56. The outer end $52_2$ of seal 52 is smooth and of cylindrical shape. The upper and lower ends of the adapter 50 are modified with inlet means for attachment to a suitable container, for ingress of a fluid specimen, and outlet means for egress of fluid specimen, as when a fluid specimen is withdrawn from the container prior to the time that it is trapped and retained within said adapter.

Continuing the reference to FIG. 4, there is shown a suitable cylinder 010, optionally provided with a safety-relief valve 01, and shut-off valves 02,03 installed on the upper and lower ends, respectively, of the cylinder. Suitably, the threaded upper end of the adapter 50 is adapted for threadable engagement with the externally threaded nipple portion of an on-off or shut-off valve 03 secured to the lower end of a container 010, and the lower threaded end of adapter 50 is thus adapted for threadable engagement with the externally threaded nipple portion of an on-off or shut-off valve 07.

The C-frame 20, characterized in FIG. 4, is identical in structure to that previously described by reference to FIGS. 1 and 2, as is the syringe 30. The normal steps involved in sampling a fluid specimen from a source contained at sub-atmospheric or supra-atmospheric pressure, and for effecting its analysis, are described generally as follows:

The container 010 is conveniently transported from the place of sample collection to a place of storage, or immediate analysis, as may be desired. Suitably, to collect a fluid specimen the container 010 is used without immediate attachment thereto of any of the other portions of the apparatus.

To collect a fluid specimen within the container 010, valve 03 is closed and valve 02 is opened to a source of fluid, liquid or gas contained at sub-atmospheric or supra-atmospheric pressure. The caps 53,54 are at this time left in place covering the seal features 51,52 to prevent possible damage, since these features are not used in securing a sample. Valves 02,03 are closed, and valve 02 is attached to a source from which the fluid specimen is to be taken. Valve 02 is then opened, this permitting the fluid (liquid or gas) to flow into and fill the container. Valve 02 is then closed, and the container 010 thus filled can be removed from the source and transported to a place for storage, or immediate analysis.

In analysis, adapter 50 is attached to container 010 via engagement with valve 03, and valve 07 is attached upon the lower end of the adapter 50. Valve 07 is closed, and while valve 02 remains closed, valve 03 is opened. This permits fluid to flow into and fill the adapter 50. Where the container 010 is filled with a liquefied gas, and preferably with any liquid, the cylinder is pressurized at about 50 psi above the vapor pressure of the fluid specimen contained in the cylinder. Caps 53,54 are unscrewed and removed to expose the seals 51,52. C-frame 20 is fitted upon the adapter 50 via loosening set screws 1,22, fitting the open end of the projecting portion 12 of holder 24 upon the smooth outer end $52_2$ of seal 52, fitting the handle portion $51_2$ of the plunger into the opening $21_1$, and then tightening down the set screws 1,22. The needle syringe 30 is inserted within seal 52 and locked in place within the holder 24 of C-frame 20. Thumb screw 22 of C-frame 20 is loosened, retracted, and the C-frame 20 moved to insert the dispensing end of the needle of syringe 30 within the fluid contents of the adapter unit 50. The thumb screw 22 is again tightened to hold the C-frame in its new position. A specimen is withdrawn into, and locked with, the barrel of the syringe 30. The thumb screw 22 is again loosened and the C-frame returned to its starting position. The thumb screw 22 is again tightened to lock the C-frame in position, the syringe 30 is unlocked from holder 24, and withdrawn. The C-frame 20 and adapter 50 can then be disassembled from the container 010 by reversal of the order of steps employed in the assembly of the apparatus.

The apparatus of the present invention can be constructed of conventional materials, suitably those substantially inert to action by the fluid, or contaminating elements. The valves and container, the fittings therefor, and the injector guide assembly are principally of metal, and can be conveniently constructed of various metals, e.g., ferrous metals such as iron, iron alloys, steel, stainless steel, and the like; or, e.g., brass, copper, bronze, chrome, and the like. The materials can be of solid or laminar construction, and can be provided with a protective film, coated, plated, or the like; particularly, those unreactive or impervious to known chemicals contained in the sample fluid. The seals of the several components constituting the apparatus can be constructed of semi-rigid forms of plastics, such material being particularly desirable in the construction of the tubular sealing components. The self-lubricated plastics are especially preferred in this capacity. The polyfluorinated ethylene polymers, notable among which is polytetrafluoroethylene (Teflon), are particularly outstanding.

It is apparent that various changes, such as in absolute or relative dimension of the parts, materials used and the like, as well as the suggested mode of taking samples, can be made without departing the spirit and scope of the invention, as will now be apparent to those skilled in the art.

Having described the invention, what is claimed is:

1. An adapter unit for the receipt and containment of a fluid specimen sampled from a source at sub-atmospheric or supra-atmospheric pressure, useful in facilitating transfer of the fluid specimen from said adapter unit to apparatus comprising a valved needle syringe, which adapter unit comprises:
   a tubular member formed by a wall which surrounds a void within which fluid can be contained, the wall of which is fitted with oppositely disposed tubular seals, each of which contains an axial opening therethrough, and through the axial openings in at least one of which is mounted a reciprocable plunger,
   a C-shaped frame one end of which can be secured to a side of the reciprocable plunger mounted within the tubular seals of the tubular member, and the other end of which is provided with a holder within which the needle syringe can be placed, and held such that the needle portion thereof can be partially inserted into the axial opening of a seal adjacent the non-secured end of the reciprocable plunger of the tubular member which also lies therein,
   means for receipt of a fluid specimen from the source, and means for containing the fluid specimen within the void of said tubular member,
   whereby movement of the C-frame will shift the plunger and holder in unison such that the plunger will be moved from the axial opening of one of the seals by the needle portion of the syringe, immersed within the fluid specimen of the tubular member, whereupon a fluid specimen at source pressure can be withdrawn, locked and stored within the syringe for subsequent injection.

2. The adapter unit of claim 1 wherein the tubular member is a container, the tubular seals are fitted within the wall of the container, the seals are constituted of a plastic material, and are contained within enclosing metal members affixed, and sealed within, the wall of the container.

3. The adapter unit of claim 2 wherein the plastic material is Teflon.

4. The adapter unit of claim 2 wherein the container is of cylindrical shape, and provided with one or more valves for ingress and egress of fluid.

5. The adapter unit of claim 4 wherein valves are located at each end of the cylindrical container such that a pressurized fluid specimen can be taken from a source, contained and the adapter unit transported.

6. The adapter unit of claim 1 wherein the tubular seals are constituted of plastic, the seals are contained within enclosing metal members affixed, and sealed, within the wall of said tubular member, and said metal members are externally threaded for receipt of open end internally threaded caps, threadably engageable therewith for protection of these members on disengagement of the C-frame from said tubular member.

7. The apparatus of claim 6 wherein the caps are fitted with chains, an end of which is secured to the tubular member.

8. The adapter unit of claim 1 wherein one end of the tubular member is operatively engageable via a shut-off valve with a valved container, the other end of the tubular member is provided with a shut-off valve, the holder portion of the C-shaped frame is of tubular shape, a forward portion thereof is slidably fitted upon a projecting end of a metal member mounted within the wall of the tubular member and within which the tubular seal is contained, and the rearward end of the holder is enlarged for receipt of the forward end of the syringe which can be locked therein after insertion of the dispensing end of the needle into the seal within the wall of the tubular member.

9. The adapter unit of claim 8 wherein the wall of the holder is notched for locking engagement with a suitable projection located on the forward end of the syringe, said projection being located on said syringe for such purpose.

10. The adapter unit of claim 1 wherein the C-frame is adjoined to the plunger via an enlarged plunger head, and the enlarged plunger head is extended into an internally threaded opening wherein it is held by a side mounted set screw, and the positioning of the plunger is adjustable by a second set screw adjustably mounted directly within the internally threaded opening via treadable engagement within said opening.

* * * * *